United States Patent [19]
Dyer

[11] Patent Number: 4,876,880
[45] Date of Patent: Oct. 31, 1989

[54] DENSIMETER

[75] Inventor: Gerald P. Dyer, Enfield, Conn.

[73] Assignee: United Technologies Corporation, Hartford, Conn.

[21] Appl. No.: 262,392

[22] Filed: Oct. 25, 1988

Related U.S. Application Data

[62] Division of Ser. No. 51,887, May 20, 1987, Pat. No. 4,809,499.

[51] Int. Cl.$^4$ ............................................. G01N 9/00
[52] U.S. Cl. ................................................... 73/32 R
[58] Field of Search ............ 73/32 R, 861.01, 861.02, 73/861.03, 861.04, 861.52, 861.61, 861.62

[56] References Cited
U.S. PATENT DOCUMENTS

| | | | |
|---|---|---|---|
| 3,726,086 | 4/1978 | Herbstritt | 60/39.28 |
| 4,078,378 | 3/1978 | Gold | 60/39.28 |
| 4,199,003 | 4/1980 | Goldsmith | 73/54 |
| 4,277,832 | 7/1981 | Wong | 364/510 |
| 4,419,898 | 12/1983 | Zanker et al. | 73/861.02 |
| 4,508,127 | 4/1985 | Thurston | 137/8 |
| 4,523,477 | 6/1985 | Miller | 73/861.02 |

Primary Examiner—John Chapman
Assistant Examiner—Michele Simons
Attorney, Agent, or Firm—Lloyd D. Doigan

[57] ABSTRACT

A densimeter is provided having a pump which impels a liquid at a constant volume through a fixed orifice. A pressure transducer measures the pressure drop of liquid across the orifice and sends a signal to a microprocessor. A microprocessor determines the density of the liquid which is equal to the pressure drop divided by a constant times the square of a volumetric flow impelled by the pump.

1 Claim, 1 Drawing Sheet

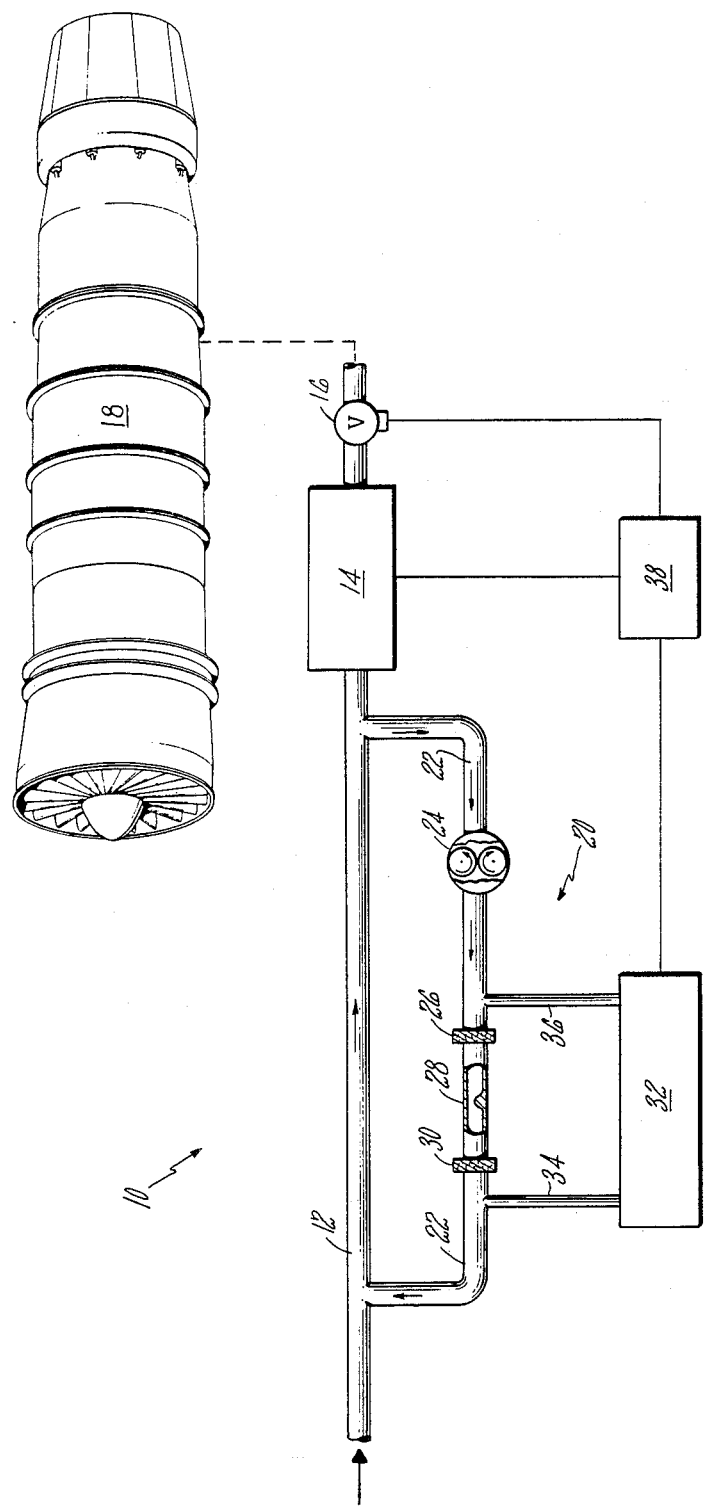

DENSIMETER

This is a division of copending application Ser. No. 051,887, filed 5/20/87, now U.S. Pat. No. 4,809,499.

TECHNICAL FIELD

The present invention relates to fuel metering systems, and more particularly, to a fuel metering system which incorporates a meter that measures fuel density.

BACKGROUND ART

In jet engine fuel metering sytems, it is desirable to control the mass flow of fuel to the engine. Most meters which measure mass flow are complicated and heavier than available volumetric flow meters. Volumetric flow meters are generally lighter, simpler and more reliable than mass flow meters. However, a fuel metering system utilizing a volumetric flow meter requires that the fuel density be known so that a true mass flow may be calculated.

DISCLOSURE OF THE INVENTION

It is, accordingly, an object of this invention to determine fuel density in a simple, reliable manner.

It is a further object of the invention to provide a simple, reliable fuel metering system.

According to the invention, a densimeter is provided which impels a constant volumetric fuel flow through a fixed orifice of known area. The densimeter includes a transducer which measures a pressure drop across the orifice so that fuel density may be calculated.

Further according to the invention, a fuel metering system is provided which includes the densimeter, a volumetric flow meter, a metering valve and a microprocessor.

The foregoing, and other features and advantages of the present invention, will become more apparent in light of the following detailed description and accompying drawing.

BRIEF DESCRIPTION OF THE DRAWING

The drawing is a schematic view of the fuel metering system of the invention.

BEST MODE FOR CARRYING OUT THE INVENTION

Referring to the drawing, an embodiment of a fuel metering system 10 is shown. Generally, fuel is impelled through a conduit 12. The conduit passes through a volumetric flow meter 14 and a metering valve 16 which meters the flow to a gas turbine engine 18. The metering valve meters fuel to the engine as a function of the volumetric fuel flow and the density of the flow. The density of the fuel is determined by a densimeter 20.

A line 22 branches off the conduit to provide fuel to the densimeter 20 and to return the fuel to the conduit after the density of the fuel is calculated. The densimeter consists of a pump 24 (as is well known in the art) which impels the fuel at a constant volumetric flow through a filter 26, a fixed orifice 28 of known area, and a second filter 30 downstream of the orifice. A transducer 32 (as is well known in the art) compares the pressure upstream and downstream of the orifice via lines 34, 36. The transducer transmits a signal to a microprocessor 38 (as is well known in the art) where the density of the fuel is calculated according to the following equation:

$$\rho = \Delta P / (K Q^2)$$

where
$\rho$ = density in pounds per cubic inch
$\Delta P$ = pressure drop across the orifice
$K$ = constant
$Q$ = volumetric flow passing from the pump.

The volumetric flow meter determines the flow of the fuel and inputs such information to the microprocessor 38.

The microprocessor may then calculate mass flow as a function of the input from the volumetric flow meter and the densimeter according to the equation:

$$W_F = \rho V$$

where
$W_F$ = mass flow in pounds per second
$\rho$ = density in pounds per cubic inch
$V$ = volumetric flow in cubic inches per second The microprocessor may then use the mass flow data to accurately position the metering valve to meter the mass flow of fuel to the engine as required.

While the present invention has been illustrated and described with respect to a particularly preferred embodiment thereof, it will be appreciated by those skilled in the art, that various modifications to this system may be made without departing from the present invention. Specifically, the densimeter may have other applications besides fuel metering. For instance, the densimeter may be particularly useful in scientific experimentation, in the packaging industry, or where ever the density of a fluid must be known. Thus it will be understood that the following claims cover the embodiment described herein and all such equivalent thereof as fall within the true spirit and scope of this invention.

Having best described the invention, what is claimed is:

1. Apparatus for determining the density of a liquid characterized by:
   means for impelling a liquid at a constant volumetric flow along a flow path;
   an orifice having a fixed area disposed within said flow path, said liquid flowing through said orifice;
   means for determining a pressure drop of said liquid across said orifice and for sending a signal corresponding to said determined pressure drop; and
   means for receiving said signal and determining said density of said liquid as a function of said pressure drop wherein said density is equal to the pressure drop divided by a constant times said square of the volumetric flow.

* * * * *